United States Patent [19]

Chvapil

[11] Patent Number: 4,777,943

[45] Date of Patent: Oct. 18, 1988

[54] USE OF TRANSPARENT MEMBRANES MADE OF HYDROGEL POLYMERS AS A COVER FOR VARIOUS ORGANS DURING SURGERY

[75] Inventor: Milos Chvapil, Tucson, Ariz.

[73] Assignee: Malliner Laboratories Inc., Edmonton, Canada

[21] Appl. No.: 929,174

[22] Filed: Nov. 10, 1984

[51] Int. Cl.$^4$ ............................................. A61F 13/00
[52] U.S. Cl. .................................... 128/850; 128/156; 128/853
[58] Field of Search ................ 128/132 R, 132 D, 156

[56] References Cited

U.S. PATENT DOCUMENTS

| | | | |
|---|---|---|---|
| 3,236,370 | 2/1966 | Pereny et al. | 128/132 D |
| 3,916,887 | 11/1975 | Kelly et al. | 128/132 D |
| 4,275,719 | 6/1981 | Mayer | 128/132 D |
| 4,340,731 | 7/1982 | Colombo et al. | 128/156 X |
| 4,362,841 | 12/1982 | Minatono et al. | 128/156 X |
| 4,377,160 | 3/1983 | Romaine | 128/156 |
| 4,486,488 | 12/1984 | Pietsch et al. | 128/156 X |
| 4,522,997 | 6/1985 | Schmitz et al. | 128/156 X |
| 4,601,286 | 7/1986 | Kaufman | 128/155 X |

*Primary Examiner*—Robert E. Bagwill
*Attorney, Agent, or Firm*—Cahill, Sutton & Thomas

[57] ABSTRACT

The object of this invention is to use a variety of thin membranes, 1.0 to 2.0 mm thick made of any hydrogel polymer, as a temporary cover on organs exposed to air during surgery. The membranes are characterized by a high water content in excess of 85 weight percent, unique biocompatibility, transparency and pliability. These characteristics prevent drying of the organ surface and reduce bacterial contamination of the exposed tissue.

7 Claims, No Drawings

USE OF TRANSPARENT MEMBRANES MADE OF HYDROGEL POLYMERS AS A COVER FOR VARIOUS ORGANS DURING SURGERY

BACKGROUND INFORMATION

The exposure of an organ to air, heat induced by the surgical illuminating lamps, and the environmental atmosphere causes drying of the organ surface and bacterial contamination of the surgical area. One of the principles for reducing risk to the organ during surgical intervention is to keep the tissue moist thus preventing drying of the organ surface. The loss of moisture at the organ surface results in cell death followed by enhanced tissue inflammatory reaction with the possibility of adhesions forming between the tissues involved. This risk is especially harmful to organs and tissues that do not have the capacity to regenerate their cells and where the tissue function relates intimately with the structure-function of the cells. Neurosurgical procedures involving the central nervous system, brain, or spinal cord, require continuous wetting of the organ surface. This also applies to surgeries involving the pancreas and intestines where the dry organ surface complicates, by well established pathogenic mechanisms, the postoperative outcome. These adverse effects can be reduced by covering exposed organs with surgical pads soaked in sterile saline or sterile Ringers solution. The disadvantage of this procedure, as currently followed, is that the gauze pad is not transparent thus prohibiting continuous inspection of the organ. The pad may also be in the way of the instruments, i.e., scalpel, scissors, etc.

In surgeries requiring retraction of the incised tissue by metallic retractors the pressure exerted by the instruments, especially during lengthy surgeries (several hours), may be detrimental to the viability of the tissue. In order to minimize the harmful effect of the pressure, a pad of wet gauze is commonly placed underneath the retractor to form a cushion between the tissue and the metal.

When instruments exert pressure on tissues, blood flow is restricted thus creating a poor oxygen supply. Also, mechanical disruption of tissue cells occurs not only with retractors, but with forceps, hemostats and instruments used mainly to compress a tubular organ, such as intestines, vessels, or esophagus. The surgeon generally places a plastic tube over the metal part of the instrument in order to reduce the compressing trauma to the tissue. However, such a plastic has no or minimal plasticity to function as a cushion.

GENERAL DESCRIPTION OF THE INVENTION

A thin membrane made of a highly biocompatible hydrogel based on polyurethane, polyacrylonitrile, or any hydrophilic polymer will need to: (a) swell in an aqueous media to contain more than 85 weight percent fluid, (b) have sufficient mechanical strength, (c) be transparent when hydrated, and (d) be nontoxic. These functions will (a) prevent drying of the exposed organ surface, (b) minimize the risk of bacterial contamination of the surgical wound, and (c) facilitate the operation because of its transparency. Due to its pliability and high fluid content, it will closely adhere to the organ surface. The composition of the membranes also allows for direct cutting through the membrane with a scalpel. If retraction of the operating field is required, the swollen membrane, with its unique viscoelastic properties, can be used as a cushion to reduce the pressure of the metal retractors on the compressed tissue.

The original membrane exists as a dry, thin sheet, and can be sterilized by any conventional method, i.e., irradiation, ethylene oxide, or even by dry heat. At the time of surgery, the sterile, dry membrane is submerged in a sterile saline or Ringers solution, and within five to ten minutes swells to contain approximately 85 to 92% water. After hydration, the membrane becomes transparent, flexible, pliable, and conforms to the uneven wet surface of any organ. The incision into the organ can be made through the membrane without any fluid leaking out of the membrane; still, the high fluid content prevents drying of the tissue.

Besides neurosurgical uses, this type of hydrogel membrane can be used in any type of surgery that requires protection of organ cells. Abdominal surgery to isolate and/or to wall off the small intestine from the operative field is another very common example.

The soft membrane placed over the surgical site also reduces the pressure exerted on the tissue by retractors or similar instruments. Also, hydrogel tubing can be slipped over retractors, hemostats or any surgical tools to reduce the pressure of the metal on the tissue.

The hydrophilic polymers we found suitable to form the above characterized thin membranes with high fluid content, yet being mechanically strong enough to prevent rupture or breaking during handling, have been the subject of various U.S. Patents and, in principle, are made of urethane or acrylonitrile. Examples of these patents using hydrogel based on polyurethane are U.S. Pat. No. 3,822,238 (issued July 2, 1974, Blair and Hudgin), U.S. Pat. No. 3,975,350 (issued Aug. 17, 1976, Hudgin and Blair), U.S. Pat. No. 4,454,309 (issued June 12, 1984, Gould and Johnston). Examples of patents using polyacrylonitrile as hydrophilic polymer are U.S. Pat. No. 4,420,589 (issued Dec. 13, 1983, Stoy) U.S. Pat. No. 4,369,294 (issued Jan. 18, 1983, Stoy) or U.S. Pat. No. 4,379,874 (issued Apr. 12, 1983, Stoy).

OBJECTS OF THE INVENTION

It is the object of this invention to document that when membranes made of any hydrophilic polymer, that will swell in an aqueous environment to retain more than 80 weight percent water, are placed over a surgically exposed organ, drying of the surface is prevented.

Another object of this invention is to characterize the optimal physical properties of hydrogel membranes that are used as temporary organ cover during surgery.

Another object of this invention is to demonstrate the method of detecting by X-ray the membrane left in the body.

Another object of this invention is to show the hydrogel being used as a cover for surgical instruments.

DESCRIPTION OF THE PREFERRED EMBODIMENTS

The following examples serve to illustrate the practice of the invention but are not to be regarded as limiting.

EXAMPLE 1

This example indicates some of the physical characteristics of membranes made of hydrophilic polymers based on polyurethane and polyacrylonitrile. Both types of membranes were incubated for 24 hours at 20° C. in 0.9 weight percent sodium chloride. The results of various determinations are shown in the Table 1.

TABLE 1

SOME PHYSICAL CHARACTERISTICS OF
HYDROGEL MEMBRANES USED AS
A TEMPORARY ORGAN COVER DURING SURGERY

| Parameter | Hydrogel of Polyurethane (D11, RL 85-86B) | Hydrogel of Polyacrylonitrile (HYPAN) |
| --- | --- | --- |
| Thickness-fully hydrated (mm) | 1.5 | 1.7 |
| Water content (weight %) | 92.3 | 83.0 |
| Young's Modulus (psi) | 0.835 | 0.623 |
| Tensile Strength (g/sq cm) | 170.3 | 111.0 |
| Elongation (in % of original length at breaking point) | 290 | 185 |
| Propagation of tear | minimal | easy |
| Color | transparent | transparent |
| Eluates into saline | none | none |

The results in Table 1 indicate that, inspite of higher fluid binding, the polyurethane membrane still had superior mechanical strength when compared to the polyacrylonitrile membrane. Other characteristics of both membranes were comparable.

EXAMPLE 2

This example illustrates the rate of fluid binding by a dry membrane made of a polyurethane hydrophilic polymer.

A dry, heat sterilized, membrane made of polyurethane D-11 polymer was immersed into 0.9 weight percent sodium chloride at temperature of 20° C. At various time intervals the water content, size change and thickness change of the membrane was measured. The results, shown in Table 2 indicate that the final swelling, size and thickness is reached at 30 minutes of incubation in the solution. Thus, the surgeon needs to submerge the sterile membrane into any sterile solution of electrolytes at least 30 minutes before covering the surface of an exposed organ with the fully hydrated membrane. However, if the membrane is packaged in solution, it can be used immediately. Note that during swelling the area size increases four times, thus the length of the membrane more than doubles.

TABLE 2

CHANGES IN SWELLING, AREA SIZE AND
THICKNESS OF THE POLYURETHANE
MEMBRANE INCUBATED IN SALINE AT 20° C.

| Time of Incubation (minutes) | Swelling (% change) | Size Area (% change) | Thickness (% change) |
| --- | --- | --- | --- |
| 0 | 100 | 100 | 100 (0.15 mm) |
| 2.5 | 543 | 311 | 160 |
| 7.5 | 683 | 381 | 190 |
| 15.0 | 729 | 380 | 227 |
| 30.0 | 752 | 457 | 220 |
| 60.0 | 749 | 459 | 223 |

The data refer to membrane D-11, RL-77-76B

EXAMPLE 3

This Example demonstrates that the brain surface exposed after the craniotomy will remain wet during four hours exposure to air only when it is covered with a hydrogel membrane.

Dogs were anesthetized with halothane passive inhalation and shaved on the dorsal aspect of the skull. After preparation of the surgical area, the skin incision and skull exposure with complete craniotomy were achieved by using a cranial reciprocating saw. Bleeding was controlled with bone wax. Dura mater was partially excised and retracted to expose approximately 30 sq cm of brain surface to the air. In some dogs the area was left intact and covered with a polyurethane hydrogel membrane. In other dogs the area was soaked in sterile saline for 30 minutes at room temperature. The membrane obtained was a dry, 0.45 mm thick layer, 7×7 cm in size, and packaged in two plastic bags. It was sterilized by dry heat at 100° C. for 90 minutes. Before the actual surgery began, the surgical nurse opened the outer bag and dropped the sterile inside bag containing the membrane onto the surgical table. The surgeon opened the inside bag and submerged the membrane in sterile Ringer's lactate solution. After 30 minutes the swollen membrane, containing 92 weight percent fluid, was used. The size of the hydrated membrane doubled from the original 7×7 cm area to a 14×14 cm area. The thickness of the membrane increased by 155% to 1.15 mm. At various time intervals the surface moisture of the exposed organ was visually estimated.

It was found that without a cover the brain surface dried within 15 minutes after exposure to the air and environment of the surface theatre. The brain surfaces covered with a hydrogel membrane remained moist for the four hour duration of the experiment. Water content of the membrane decreased from the original 92 weight percent to 74 weight percent fluid during this four hour experiment. We conclude that covering the brain tissue with the hydrogel membrane completely prevented the drying of the exposed organ during the four hour surgery.

What is claimed is:

1. A method of protecting surgically exposed moist tissue, comprising the steps of:
   (a) providing a thin membrane of dry, sterile hydrophilic polymer hydrogel which can absorb at least about 80 weight percent immobilized water, and which is transparent, pliable, and soft when saturated with water;
   (b) submerging the membrane in sterile aqueous solution until the membrane swells and absorbs enough water that it is composed of at least about 80 weight percent immobilized water;
   (c) placing the membrane on the moist tissue so that the membrane conforms to the shape of the moist tissue, the membrane maintaining the moistness of the tissue; and
   (d) visualizing the moist tissue through the membrane and simultaneously making an incision through the membrane into the moist tissue, the membrane retaining water and preventing drying of the moist tissue in contact with the membrane and preventing exposure of the moist tissue to bacterial contamination.

2. The method of claim 1 including positioning part of the membrane between a retractor and the moist tissue to reduce pressure exerted on the tissue by the retractor.

3. The method of claim 1 including attaching a radiocontrast material to the membrane.

4. The method of claim 1 wherein the hydrophilic polymer hydrogel is from the group consisting of polyurethane and polyacrylonitrile.

5. A method of preventing cell damage in surgically exposed tissue due to pressure on the tissue by metallic portions of a surgical instrument, comprising the steps of:

(a) forming a tube of dry, sterile biocompatible hydrophilic polymer hydrogel composed of material from the group consisting of polyurethane and polyacrylonitrile, the polyacrylonitrile and polyurethane being pliable and soft when saturated with water;

(b) submerging the tube in sterile aqueous solution until the tube swells and absorbs enough water that it is composed of at least about 80 weight percent immobilized water;

(c) placing the tube on the instrument to cover the metallic portions thereof that come in contact with the tissue to reduce pressure and other tissue-damaging effects of the surgical instrument.

6. The method of claim 5 including reversing the order of steps (b) and (c).

7. A method of using a protective membrane, comprising the steps of:

(a) providing a membrane of transparent, pliable hydrophilic hydrogel material;

(b) hydrating the membrane by immersing it in a hydrous electrolyte solution to cause it to absorb at least approximately 80 percent by weight of water;

(c) placing the membrane on an exposed portion of an organ to prevent exposure to the organ to air and bacterial contamination and to prevent drying of the exposed portion of the organ;

(d) viewing the organ through the membrane to locate a site for an incision; and (e) cutting through the membrane into the tissue of the organ at the incision site to make the incision, the membrane material adjacent to the cut through the membrane remaining in contact with the organ tissue, preventing drying of organ tissue adjacent to the incision in the organ.

* * * * *